US00PP11070P

United States Patent [19]

Cummins et al.

[11] Patent Number: Plant 11,070

[45] Date of Patent: Sep. 28, 1999

[54] APPLE ROOTSTOCK NAMED 'GENEVA 11'

[75] Inventors: James N. Cummins; Herbert S. Aldwinckle, both of Geneva, N.Y.

[73] Assignee: Cornell Research Foundation, Inc., Ithaca, N.Y.

[21] Appl. No.: 08/967,211

[22] Filed: Oct. 29, 1997

Related U.S. Application Data

[63] Continuation of application No. 08/760,293, Dec. 4, 1996, abandoned, which is a continuation of application No. 08/609,417, Mar. 1, 1996, abandoned, which is a continuation of application No. 08/353,305, Dec. 5, 1994, abandoned, which is a continuation of application No. 08/184,627, Jan. 21, 1994, abandoned.

[51] Int. Cl.[6] ..... A01H 5/00

[52] U.S. Cl. ..... Plt./174

[58] Field of Search ..... Plt./34.1, 161, Plt./173, 174, 175

*Primary Examiner*—Howard J. Locker

[57] ABSTRACT

A new and unique apple rootstock, 'Geneva 11' that is dwarfing and resistant to crown rot and fire blight.

6 Drawing Sheets

CROSS-REFERENCE TO RELATED APPLICATIONS

This application is a continuation of application Ser. No. 08/760,293, filed Dec. 4, 1996, now abandoned, which is a continuation of application Ser. No. 08/609,417, filed Mar. 1, 1996, now abandoned, which is a continuation of application Ser. No. 08/353,305, filed Dec. 5, 1994, now abandoned, which is a continuation of application Ser. No. 08/184,627, filed Jan. 21, 1994, now abandoned.

BACKGROUND OF THE INVENTION

The present invention relates to a new and distinct asexually-reproduced cultivar of apple tree, 'Geneva 11', which we discovered in a test planting belonging to New York State Agricultural Experiment Station, Cornell University, Geneva, Ontario County, N.Y. This discovery is a product of the apple rootstock breeding program of the New York State Agricultural Experiment Station ("Station").

ORIGIN

In March 1978, pollen was collected from a *Malus*× *robusta* cv. Robusta 5 apple tree and used to pollinate emasculated flowers of a *Malus*×*domestica* cv. Malling 26 (M.26) apple tree growing in Station greenhouse No. 13. The seeds were harvested from fruit produced from this cross and were stratified in November 1978. After stratification, 180 germinating seeds were planted in a Station greenhouse in January 1979. When the emerging seedlings were about 2.5 cm tall, we inoculated with 15 isolates of the fungi *Phytophthora cactorum* and *Phytophthora megasperma*, which are causal agents of certain crown and root rots. The flat was flooded to mid-hypocotyl level of the seedlings, and kept at about 23° C. for 7 days; 104 seedlings survived this treatment. The surviving seedlings, when 10 to 15 cm tall, were inoculated in their shoot tips with about $10^6$ cells of isolate Ea 273 of the bacterium *Erwinia amylovora*, the causal agent of the fire blight disease, using a 26-gauge hypodermic syringe. Four subsequent inoculations with *E. amylovora* isolate Ea 273 were made in summer and autumn, 1979. The seedling designated 7826R5-011, later tested as CG.11 and now named 'Geneva 11', was very resistant; lesions were less than 2 cm long. Later, lesions 5 cm long developed when Geneva 11 shoots were inoculated with E4001A, a very virulent strain of the bacteria. The survivors were inoculated repeatedly with woolly apple aphids (*Eriosoma lanigerum*); very susceptible individuals were discarded. The plant now designated 'Geneva 11' was moderately susceptible to woolly aphids. Seedlings with very small leaves and those displaying either root initials or spines were also discarded.

We selected 15 *Erwinia amylovora*-resistant seedlings and planted them as trench layers on the Station's Loomis Farm in April 1980. Rooted liners were harvested in late fall 1983 and were planted in the Station nursery in the spring of 1984. Maiden trees of the cultivars 'Topred Delicious', 'Summerland McIntosh' and 'Mutsu' were produced by budding the 'Geneva 11' liners. These trees were subsequently planted in trial orchards at the Station at the United Stated Department of Agriculture Appalachian Fruit Research Station, Kearneysville, W. Va., Hilltop Orchards, Hartford, Mich.; Littletree Orchards, Newfield, N.Y.; and Brown Orchards (Indian Creek Fruit Farm), Ithaca, N.Y.

In these test plantings, trees on 'Geneva 11' were similar in size to those on 'Malling 26' rootstock, based on comparison with the check trees in the same test plantings. Trees on 'Geneva 11' began flowering early, usually the 2nd or 3rd year in the orchard; this was especially noteworthy for 'Mutsu' cultivar, which in New York normally begins fruiting in the 3rd or 4th year when grafted on the precocity-inducing rootstock 'Malling 26'. All of the cultivars that have been tested on 'Geneva 11' have demonstrated high production efficiency, equal to or more than that experienced with the efficient 'Malling 26' rootstock.

COMPATIBILITY

We have observed no symptoms of incompatibility with 16 trees of the 3 fruiting cultivars mentioned above. Besides these, we have grafted 'Jonagold', 'Melrose', 'Empire', 'Gala', and 'Liberty' cultivars 'Geneva 11'; in the nursery we have observed no symptoms of incompatibility. All scionwood used was free from known harmful viruses.

PROPAGATION

We have propagated 'Geneva 11' asexually by budding and grafting onto seedling and clonal rootstocks; by root cuttings; by hardwood cuttings; by greenwood cuttings; and by conventional layering. These asexual propagules have remained true-to-type with these methods of asexual propagation. We have also propagated 'Geneva 11' readily in tissue culture; however, 'Geneva 11' appears to be especially sensitive to epigenetic changes, apparently induced by the growth regulator environment in the tissue culture medium: leaf width is significantly reduced; more and longer spines are produced in the stoolbed; shoots mature very late; susceptibilities to fire blight and to powdery mildew are increased; and rooting in the stoolbed is accelerated. In the stoolbed, these changes disappear with time. The effects described here occurred with a particular set of tissue culture events. Other tissue culture regimens, with different hormonal concentrations, different numbers of transfers and different microenvironments, have yielded different results. In general, these epigenic effects are maximized with higher concentrations of growth regulating substances in the media, and/or with prolonged culture, and/or numbers of transfers. We have no evidence they are related to juvenility. We do not consider them to be ontogenic effects. The experience thus far suggests these epigenic effects are temporary.

We have also used 'Geneva 11' as a pollen parent in our breeding program. 'Geneva 11' is considered to be highly heterozygous because its parents are very different from each other. Its seedlings are much different from both parents and from each other. No progeny testing has been carried out.

DESCRIPTION OF THE INVENTION

Following is a detailed description of our new cultivar, 'Geneva 11'. Accompanying FIGS. 1–8 depict behavior in the stoolbed and leaf and shoot characteristics. The numerical color specifications employed are those of The Royal Horticultural Society Colour Chart (1976). Botanical descriptions follow Manual of Cultivated Plants (Bailey, 1949).

TREE HABIT

Figure 5:
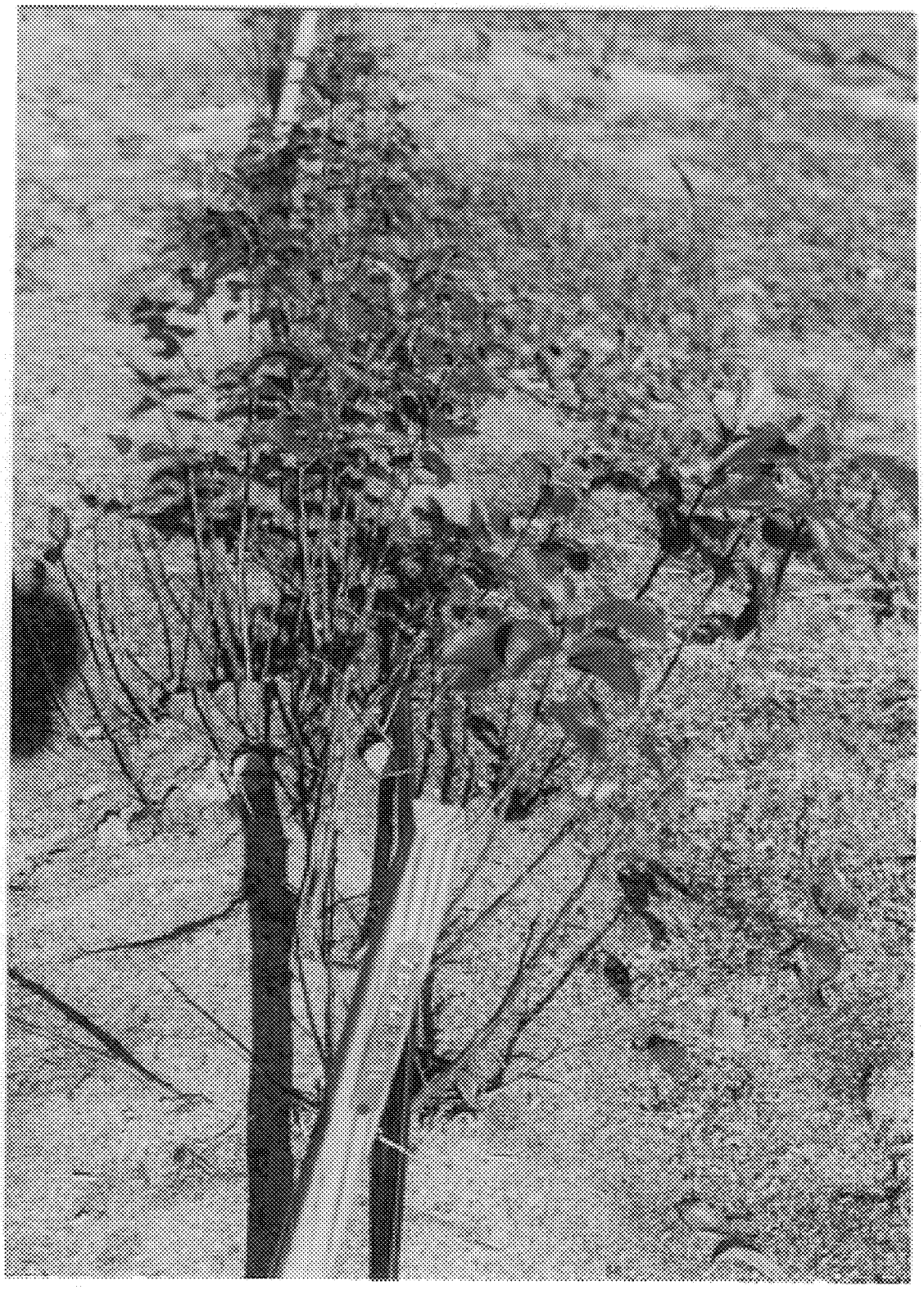
FIGS. 5 and 6 show that shoots in the layer bed are straight and 40% are clean-shanked. Several short spines occur on about half the shoots. Shoot maturation and leaf fall are moderately early.
Figure 6:
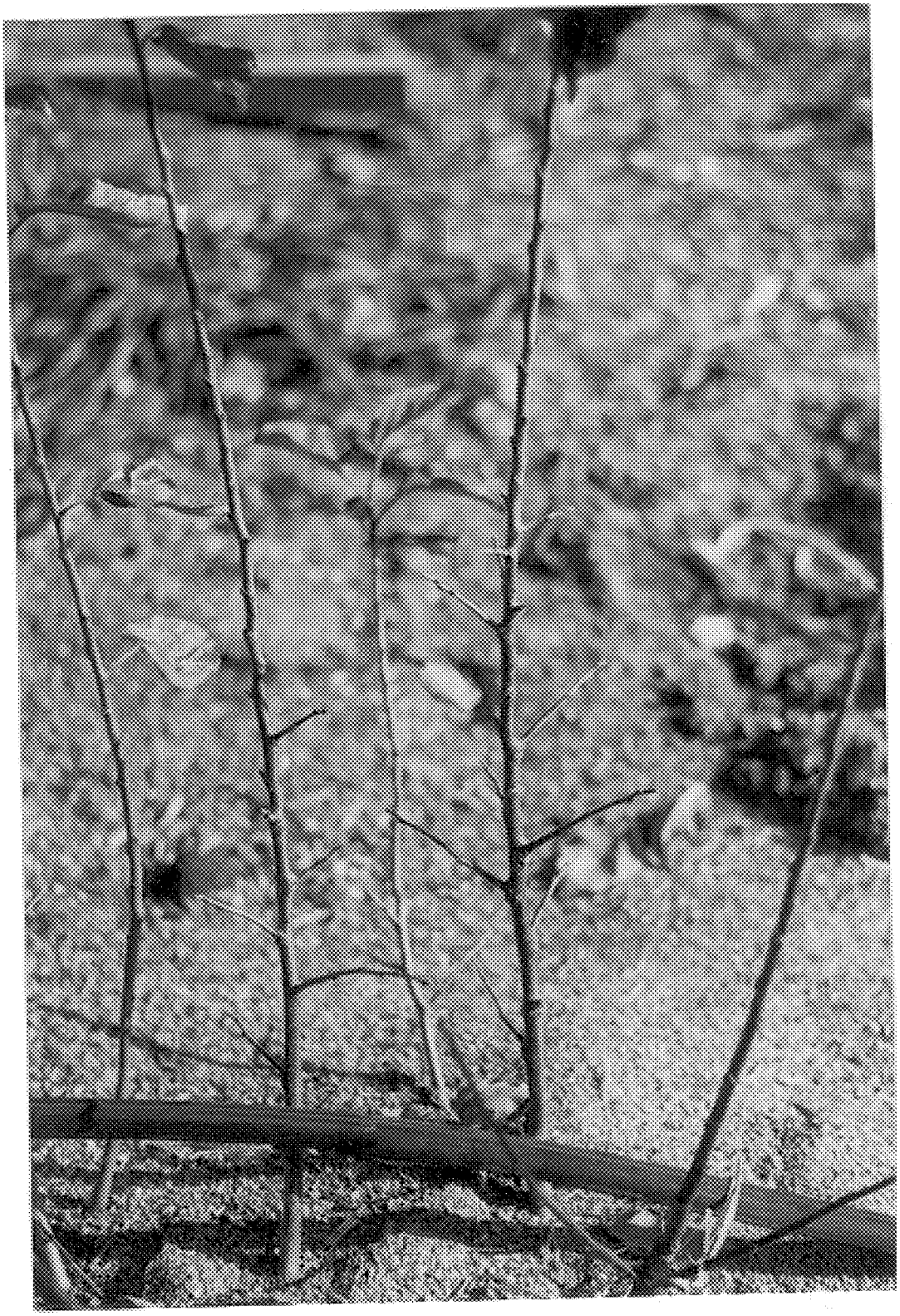
Figure 7:
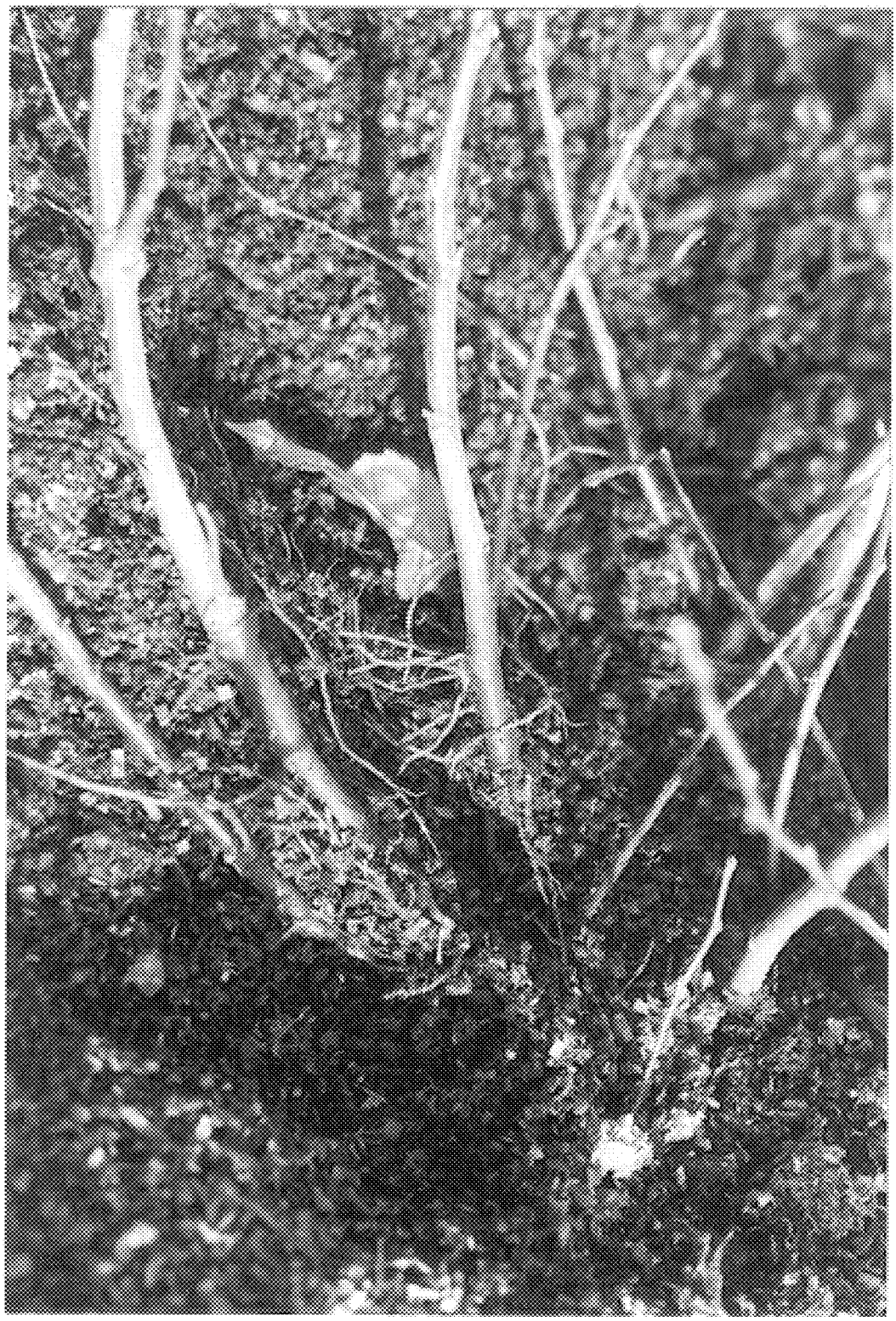
FIG. 7 shows that in the layer bed, 'Geneva 11' shoots root from the bud gap. Relatively few roots are produced; these tend to be moderately coarse, with few branches.

The unbudded tree of 'Geneva 11' is a small shrub, typically standing about 2.5 m tall×about 2 m wide. There is no single dominant trunk, but rather 4 to 8 shoots arising from the roots (FIG. 5). The unbudded tree is a dwarf, comparable to a 'Malling 26' apple tree of similar age. Growth rate is moderately slow, with early cessation of growth typically occurring about 1 week earlier than for 'Malling 26'. Spring budbreak is midseason to moderately late. Over a two to four year period, an unbudded tree may produce two to five suckers, which become multiple stocks; in contrast, the unbudded tree of 'Malling 9' produces a moderate number of suckers and there are many shoots developing into small stocks. As an unbudded plant, 'Geneva 11' is not precocious; we have not observed flowers and we have not observed fruit until December 1998. We do not know whether 'Geneva 11' is a self-fertile.

DORMANT SHOOTS

Figure 1:
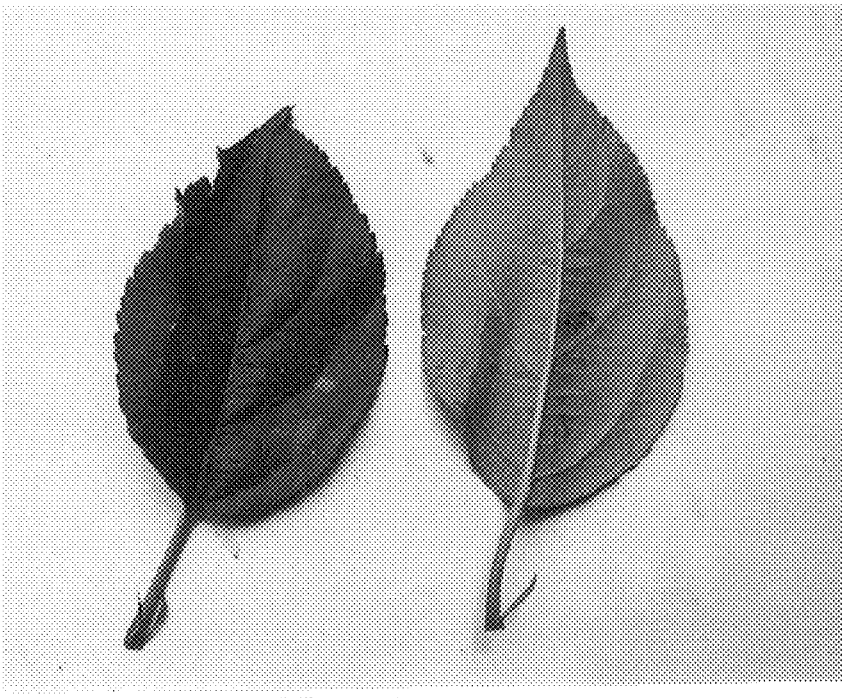
FIG. 1 is a photograph showing the topside of a 'Geneva 11' leaf and the underside of a 'Geneva 11' leaf.
Figure 2:
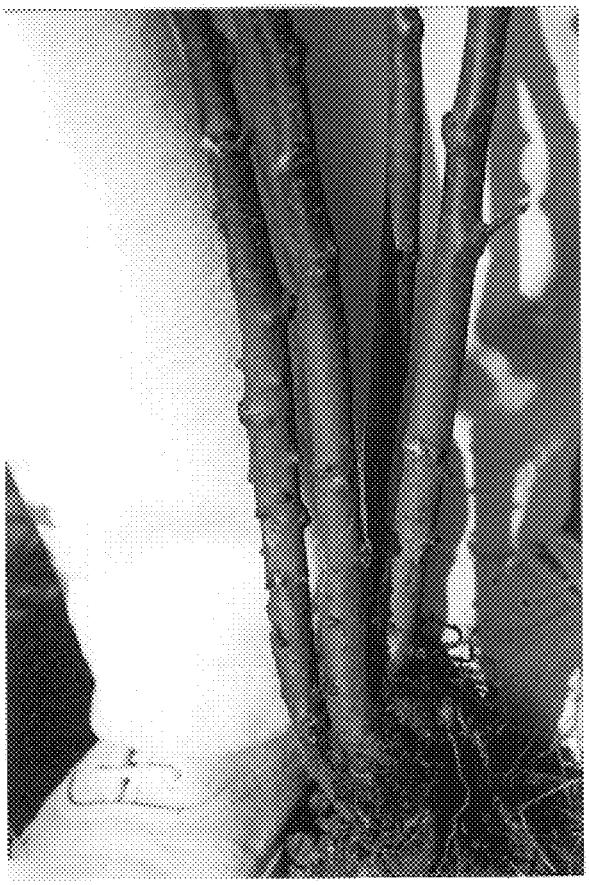
FIG. 2 is a photograph of leaves of dormant 'Geneva 11' shoots that have been etiolated in sawdust mulch through the previous growing season.
Figure 3:
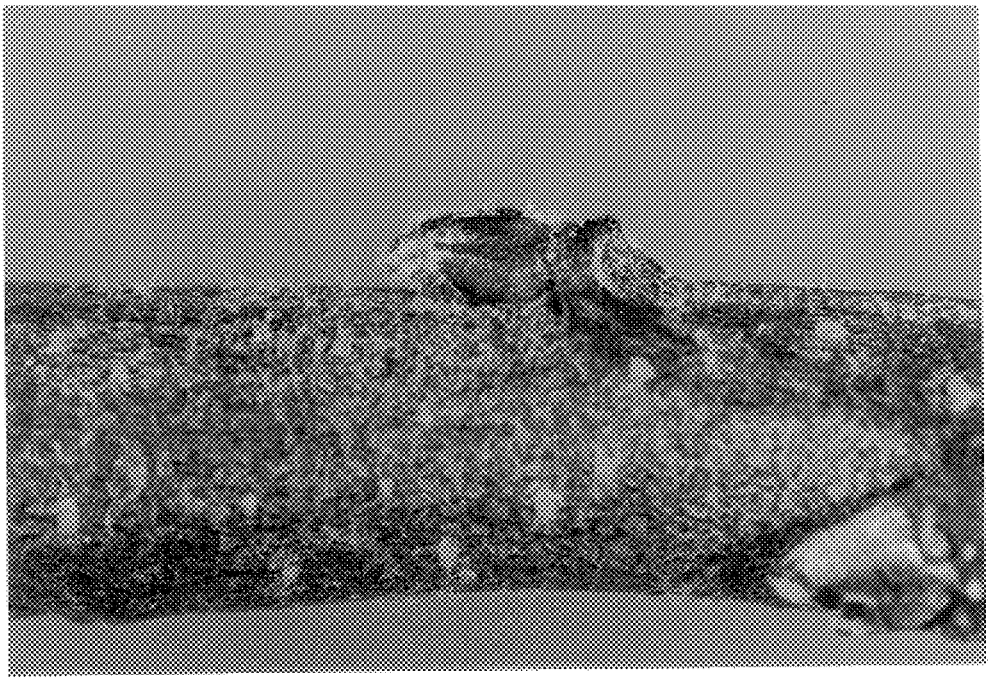
FIGS. 3 and 4 show that pubescence on dormant shoots is light. Lenticels are very slightly raised, round or nearly so, greyed orange in color. Dormant buds are obtuse, sessile, brown; a pronounced ridge is typically observed centrifugal to the median bud trace and extending about 1 mm below bud insertion.
Figure 4:
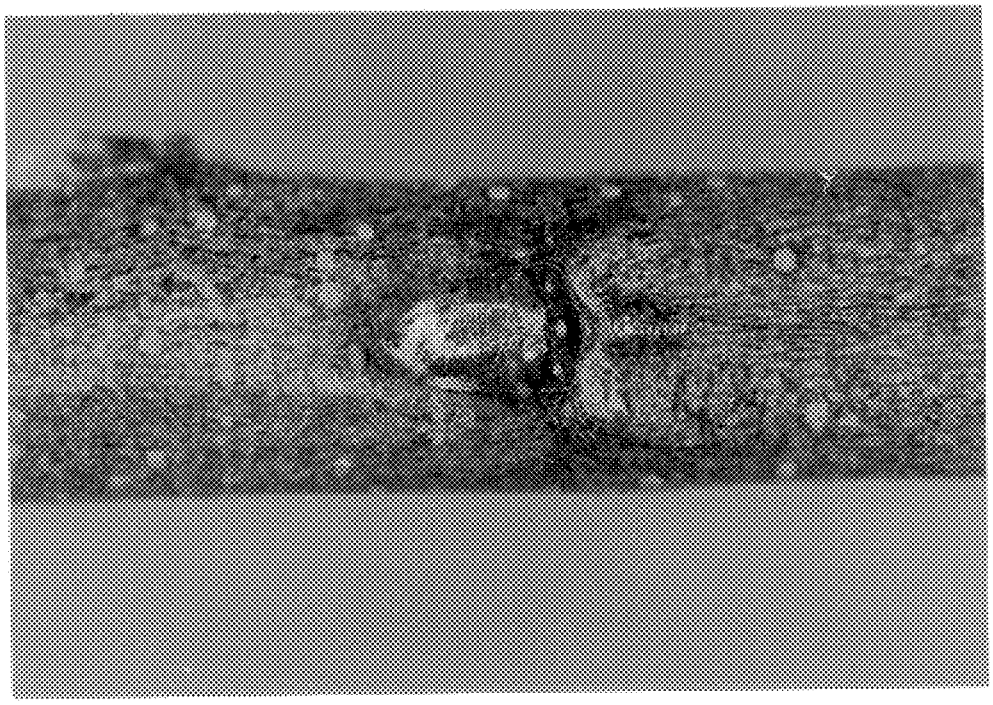
Figure 8:
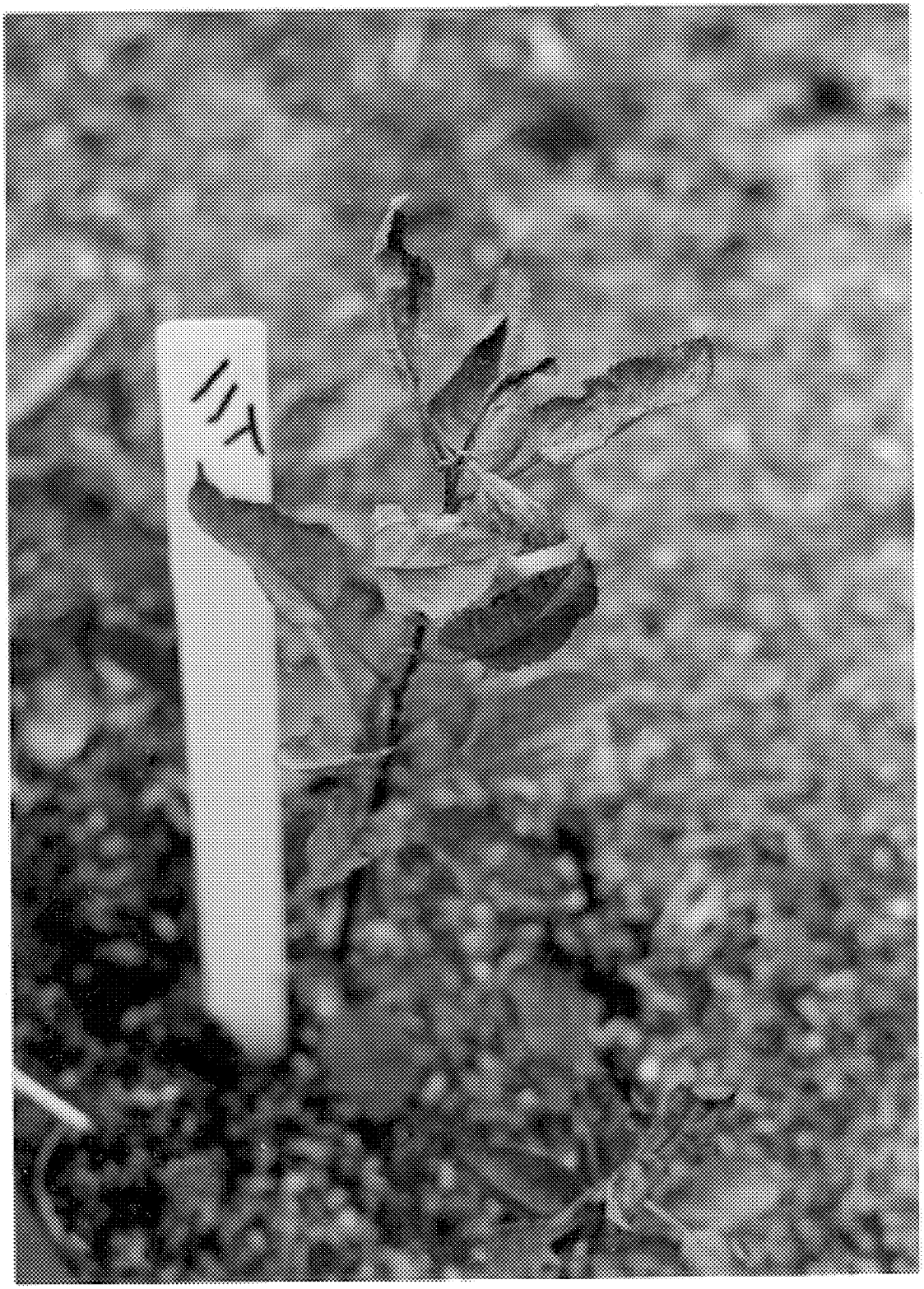
FIG. 8 shows that leaves on shoots derived from tissue culture are moderately susceptible to powdery mildew, although infection on the shoot is rare. We have not seen powdery mildew on leaves of shoots derived from normal layer bed propagation.

In the stoolbed and nursery row, dormant matured shoots of current season (one-year shoots) are Brown 200B where exposed to full sunlight, grading to grey-brown 199A and 199B with diminished light exposure (FIGS. 5 and 8). Pubescence is light (FIGS. 3 and 4). Shoots are of below average vigor, usually about 50 to 70 cm in the stoolbed. Midshoot internodes are below average, ranging from 14 to 17 mm. Profuse root primordia develop on etiolated shoot base of 'Geneva 11' and erupt both from supranodal tissue and from internodal sites (FIG. 2). Axillary buds are obtuse, sessile, usually somewhat appressed. Usually the bark surface immediately below the centrifugal to the median leaf trace exhibits a sharp 1 mm extension. The bark on one-year shoots and on two-year shoots is the same and is epidermal and therefore is not bark in the botanical meaning. Axillary buds are vegetative only. Bud scales are average size, brown 200A, with heavy greyed-white 156D pubescence at the bud tip. Lenticels are round, small in size, mostly 0.2 to 0.3 mm diameter, very slightly raised, greyed-orange 165C in midshoot section (FIGS. 3 and 4). Burrknots are not present on 1- or 2-year old shoots; a root initial occurs on about 10% of older shoots, always from the bud-gap, usually just above the basal bud scale scars. When shoots of 'Geneva 11' have been etiolated, root primordia develop both from the supranodal bud-gap tissue and randomly in internodal sites. No sphaeroblasts have been observed. Spring budbreak is early midseason, several days before 'Malling 26'. Autumn leaf-fall is moderately early, usually a week to ten days before M.26. Wood is not brittle, similar to M.26. In the stoolbed, 40% of the shoots have no spines and an additional 25% have only 1 or two; the remaining shoots averaged 6 spines per shoot; spines averaged 32 mm long. One-year-old shoots harvested from layer bed exhibit typical 2/5 phyllotaxy, and spines are present on about half of said shoots, and stipules are reduced or absent.

LEAVES

Leaves are simple; ovate and about one and one-half times long as broad (FIGS. 1 & 8); lamella somewhat wavy; tip acuminate; margin acutely serrate, usually doubly, sometimes triply; about 4 serrations per cm; base obtuse, usually slightly asymmetrical; stipules small, usually about 1×10mm. Lamellae average 75×48mm. Adaxial lemella surface green 137B; abaxial surface yellow-green 147B; upper surface nearly glabrous; short pubescence on lower surface. Petiole 20 to 25 mm long. Leaf poise typically 35° to 45° from shoot. The coloration of the veins and petioles varies with culture and climate.

FRUIT

Flowers and fruit are not normally observed on this rootstock cultivar, since all shoots are normally harvested after one season's growth. However, in an abandoned test plot in Geneva, N.Y., one two-year sucker of 'Geneva 11' was discovered bearing apples. On this plant, fruits were borne on very short spurs formed the previous year. Fruits of 'Geneva 11' are oblong-conic, 30 to 40 mm long×22 to 32 mm diameter. Skin is yellow-orange 19C with overcolor orange 24A on side exposed to sun. Peduncle is long, 22 to 30 mm, very flexible and thin, less than 1 mm diameter, non-brittle. Calyx is protuberant and closed. Flesh is fine-graned orange-white 159B. Calyx tube is closed and basin very deep. Seeds are dark brown greyed-orange 166A, 5 to 7 mm long×3 to 4 mm.

ELECTROPHORESIS

Horizontal starch gel electrophoresis was conducted on extracts from dormant lateral buds of 'Geneva 11'. The isozymes glucosephosphate isomerase (GPI), phosphoglucomutase (PGM) and 6-phosphogulconate dehydrogenase (6PGD) were used to obtain comparisons between 'Geneva 11' and its near-relative, 'Malling 9'. 'Malling 9' is the mother of 'Malling 26' which is the mother of 'Geneva 11'. 'Malling 9' is a reference clone, used worldwide in chemical identification of apple rootstocks. The GPI and PGM systems are especially useful in distinguishing among apple rootstocks derived from 'Malling 9'. The electrophoresis showed the following differences between 'Geneva 11' and 'Malling 9': The 6PGD system differentiated the two rootstocks in that 'Geneva 11' exhibits a faint but distinct band near the anode, which is absent in the case of 'Malling 9'. The GPI system differentiated the two rootstocks at three, possibly four loci in that for 'Geneva 11' there is a band closer to the anode than in the case of 'Malling 9' and the banding pattern between the bands closest to the anode and closest to the cathode is different for 'Geneva 11' compared to that for 'Malling 9'. The two clones were similar only on the bands nearest the cathode; this band appears to be similar on a very large number of Malus cultivars. In the PGM system, 'Geneva 11' exhibits a banding near the cathode just downstream from the band nearest the cathode that is absent for 'Malling 9'. The data shows that 'Geneva 11' may be distinguished from 'Malling 9' by at least five banding patterns exhibited on the isozyme systems 6-PGD, GPI, and PGM. The method of distinguishing apple rootstocks by isozyme banding patterns is described in Samimy, C. and Cummins, J. N., Hort. Science 27(7), 829–831 (1992).

USEFULNESS

'Geneva 11' is a dwarfing apple rootstock that will directly challenge the 'Malling 26' rootstock, which is susceptible to crown and root rots and very susceptible to fire blight. 'Geneva 11' survived inoculation with two of the most important incitants of crown and root rots; it may therefore have tolerance to certain crown and root rots caused by species of the Phytophthora fungus. The fire blight disease is limiting to apple production in many parts of the United States, including California, Washington, the Mid-South and the eastern seaboard states, especially when dwarfing rootstocks in the 'Malling 26' class are desired. 'Geneva 11' is moderately resistant to fire blight, and Geneva 11 will be especially valuable in those areas in which fire blight is endemic. 'Geneva 11' is moderately resistant to powdery mildew (*Podosphaera leucotrichum*) in the layerbed and nursery. We have not observed apple scab (*Venturia inaequalis*) on 'Geneva 11' but no definitive testing has been carried out. Both these diseases are of minor importance in the nursery, and foliage diseases do not appear on the rootstock in the orchard. In the orchard, anchorage of grafted trees is similar to that of trees on 'Malling 26', but because of the precocity induced by 'Geneva 11', permanent support is strongly suggested. In the budded tree in the orchard, very few suckers are produced and they are not exuberant. 'Geneva 11' will be used as a rootstock in high density plantings, mostly at densities of about 1,000 trees per hectare. We do not expect that either conventional trellis support or espalier training will be applied; trees on 'Geneva 11' do not require the level of support offered by conventional trellis, and they are usually too vigorous for espalier training. We expect that 'Geneva 11' will be extensively used in vertical axis systems and will sometimes be trained to unsupported central leaders. 'Geneva 11' has no potential as an ornamental crabapple.

What is claimed is:

1. A new and distinct cultivar of apple tree, substantially as shown and described herein, characterized particularly as to novelty by being a dwarfing rootstock that is resistant to fire blight.

* * * * *